US011903598B2

(12) United States Patent
Coyne et al.

(10) Patent No.: US 11,903,598 B2
(45) Date of Patent: Feb. 20, 2024

(54) BONE DISPLACEMENT SYSTEM AND METHOD

(71) Applicant: NEXTREMITY SOLUTIONS, INC., Warsaw, IN (US)

(72) Inventors: Matthew Coyne, Warsaw, IN (US); Gregory Denham, Warsaw, IN (US)

(73) Assignee: MEDARTIS AG, Basel (CH)

( * ) Notice: Subject to any disclaimer, the term of this patent is extended or adjusted under 35 U.S.C. 154(b) by 245 days.

(21) Appl. No.: 17/462,719

(22) Filed: Aug. 31, 2021

(65) Prior Publication Data

US 2022/0061861 A1 Mar. 3, 2022

Related U.S. Application Data

(60) Provisional application No. 63/073,205, filed on Sep. 1, 2020.

(51) Int. Cl.
*A61B 17/17* (2006.01)
*A61B 17/02* (2006.01)
*A61B 17/68* (2006.01)

(52) U.S. Cl.
CPC ........ *A61B 17/1775* (2016.11); *A61B 17/025* (2013.01); *A61B 17/1796* (2013.01); *A61B 17/68* (2013.01); *A61B 2017/681* (2013.01)

(58) Field of Classification Search
CPC .......................... A61B 17/1775; A61B 17/025
See application file for complete search history.

(56) References Cited

U.S. PATENT DOCUMENTS

| 8,764,807 | B2 | 7/2014 | Michel et al. |
| 9,421,103 | B2 | 8/2016 | Jeng et al. |
| 10,159,480 | B2 | 12/2018 | Tuten |
| 10,368,926 | B2 | 8/2019 | Johnson et al. |

(Continued)

FOREIGN PATENT DOCUMENTS

| AU | 2021200828 A1 | 8/2021 |
| IT | 201800006879 A1 | 7/2018 |
| WO | 2020041841 A1 | 3/2020 |

OTHER PUBLICATIONS

GB 2,604,414 (NEXTREMITY SOLUTIONS, INC) Sep. 7, 2022 (claims). [retrieved on Sep. 20, 2023] Retrieved from: United Kingdom patent information and document service (Ipsum) using the Internet: <URL: https://www.ipo.gov.uk/p-ipsum.htm> (Year: 2022).*

(Continued)

*Primary Examiner* — Christian A Sevilla
(74) *Attorney, Agent, or Firm* — Heslin Rothenberg Farley & Mesiti P.C.; Victor A. Cardona, Esq.

(57) ABSTRACT

A bone displacement system includes a body having a first arm and a second arm. The first arm is connected to a first leg configured to engage a plate configured to be located on a first bone portion. The second arm is connected to a second leg configured to be connected to a second bone portion. A force application fixture is coupled to the first arm and the first leg and configured to apply a force between the first arm and the first leg. The plate has screw holes aligned to allow screws to connect the plate to the first bone portion and the second bone portion after a movement of the first bone portion relative to the second bone portion by the force applied by the force application fixture.

17 Claims, 15 Drawing Sheets

(56) References Cited

U.S. PATENT DOCUMENTS

| | | |
|---|---|---|
| 10,610,241 B2 | 4/2020 | Wagner et al. |
| 2008/0188852 A1 | 8/2008 | Matityahu |
| 2009/0131987 A1* | 5/2009 | Matityahu .......... A61B 17/8019 |
| | | 606/280 |
| 2013/0178864 A1 | 7/2013 | Ushiba |
| 2013/0338781 A1 | 12/2013 | Bordeaux |
| 2017/0020537 A1* | 1/2017 | Tuten ................. A61B 17/0642 |
| 2017/0100175 A1 | 4/2017 | Dacosta |
| 2018/0214163 A1 | 8/2018 | McCormick |
| 2019/0150999 A1 | 5/2019 | Bohay et al. |
| 2021/0244443 A1 | 8/2021 | Coyne et al. |
| 2021/0369287 A1* | 12/2021 | Boffeli .................. A61B 17/66 |

OTHER PUBLICATIONS

Merete Technologies Inc., MetaStep Calcaneus: Surgical Technique and Ordering Information, pp. 1-16, Jan. 2018.
Australian Examination Report No. 1, dated Sep. 13, 2023, 7 pp.
UKIPO Search Report dated May 30, 2022, 2 pp.

* cited by examiner

BONE DISPLACEMENT SYSTEM AND METHOD

CROSS-REFERENCE TO RELATED APPLICATIONS

The present application claims priority to U.S. Provisional Application Ser. No. 63/073,205 filed Sep. 1, 2020, which is incorporated herein by reference.

The present application is related to U.S. patent application Ser. No. 17/172,672 filed Feb. 10, 2021, which claims priority to U.S. Provisional Application Ser. No. 62/972,369, both of which are incorporated herein by reference in their entirety.

FIELD OF THE INVENTION

The present invention generally relates to osteotomy, in and in particular to compression or distraction, displacement, and fixation of bone during osteotomies.

BACKGROUND

During an osteotomy surgical procedure, bone displacement may be manually performed. Current distraction techniques limit the amount of bone preparation possible and existing compression techniques often provide for an inadequate fit. Current fixation techniques involve wiring to support and maintain bone position prior to fixation, often leading to inadequate or misaligned fixation.

Thus, a need exists for better controlled displacement, distraction, compression, and fixation during osteotomy surgical procedures.

SUMMARY OF THE INVENTION

The present invention provides, in one aspect, a bone displacement system including a body having a first arm and a second arm. The first arm is connected to a first leg configured to engage a plate configured to be located on a first bone portion. The second arm is connected to a second leg configured to be connected to a second bone portion. A force application fixture is coupled to the first arm and the first leg and configured to apply a force between the first arm and the first leg. The plate has screw holes aligned to allow screws to connect the plate to the first bone portion and the second bone portion after a movement of the first bone portion relative to the second bone portion by the force applied by the force application fixture.

The present invention provides, in one aspect, a method for use in displacing a bone, which includes locating a plate on a first bone portion and coupling a first arm of a body to the first bone portion via a first leg connected to the body engaging the plate located on the first bone portion. A second arm of the body is coupled to a second bone portion via a second leg connected to the body. A force is applied between the first arm and the first leg via a force application fixture coupled to the first arm and the first leg to move the first bone portion relative to the second bone portion. The plate is attached to the first bone portion and the second bone portion via screws through openings in the plate after the moving the first bone portion relative to the second bone portion.

These, and other objects, features and advantages of this invention will become apparent from the following detailed description of the various aspects of the invention taken in conjunction with the accompanying drawings.

DETAILED DESCRIPTION OF THE INVENTION

The present invention will be discussed hereinafter in detail in terms of various exemplary embodiments according to the present invention with reference to the accompanying drawings. In the following detailed description, numerous specific details are set forth in order to provide a thorough understanding of the present invention. It will be obvious, however, to those skilled in the art that the present invention may be practiced without these specific details. In other instances, well-known structures are not shown in detail in order to avoid unnecessary obscuring of the present invention. Moreover, in the present description, the terms "upper", "lower", "left", "rear", "right", "front", "vertical", "horizontal", and derivatives thereof shall relate to the invention as oriented in FIG. 1.

The following description references systems, methods, and apparatuses for use in compression/distraction, displacement, and fixation of a calcaneal osteotomy. A calcaneal osteotomy involves the cutting and repositioning of portions of a calcaneus to correct alignment. However, those possessing an ordinary level of skill in the relevant art will appreciate that other bone osteotomies are suitable for use with the foregoing systems, methods, and apparatuses. Likewise, the various figures, steps, procedures, and work-flows are presented only as an example and in no way limit the systems, methods or apparatuses described to performing their respective tasks or outcomes in different time-frames or orders. The teachings of the present invention may be applied to compression/distraction, displacement, and fixation related to any osteotomy.

Furthermore, there is no intention to be bound by any expressed or implied theory presented in the preceding technical field, background, brief summary, or the following detailed description. It is also to be understood that the specific devices and processes illustrated in the attached drawings, and described in the following specification, are simply exemplary embodiments of the inventive concepts. Hence, specific dimensions and other physical characteristics relating to the embodiments disclosed herein are not to be considered as limiting, unless expressly stated otherwise.

Figure 1:
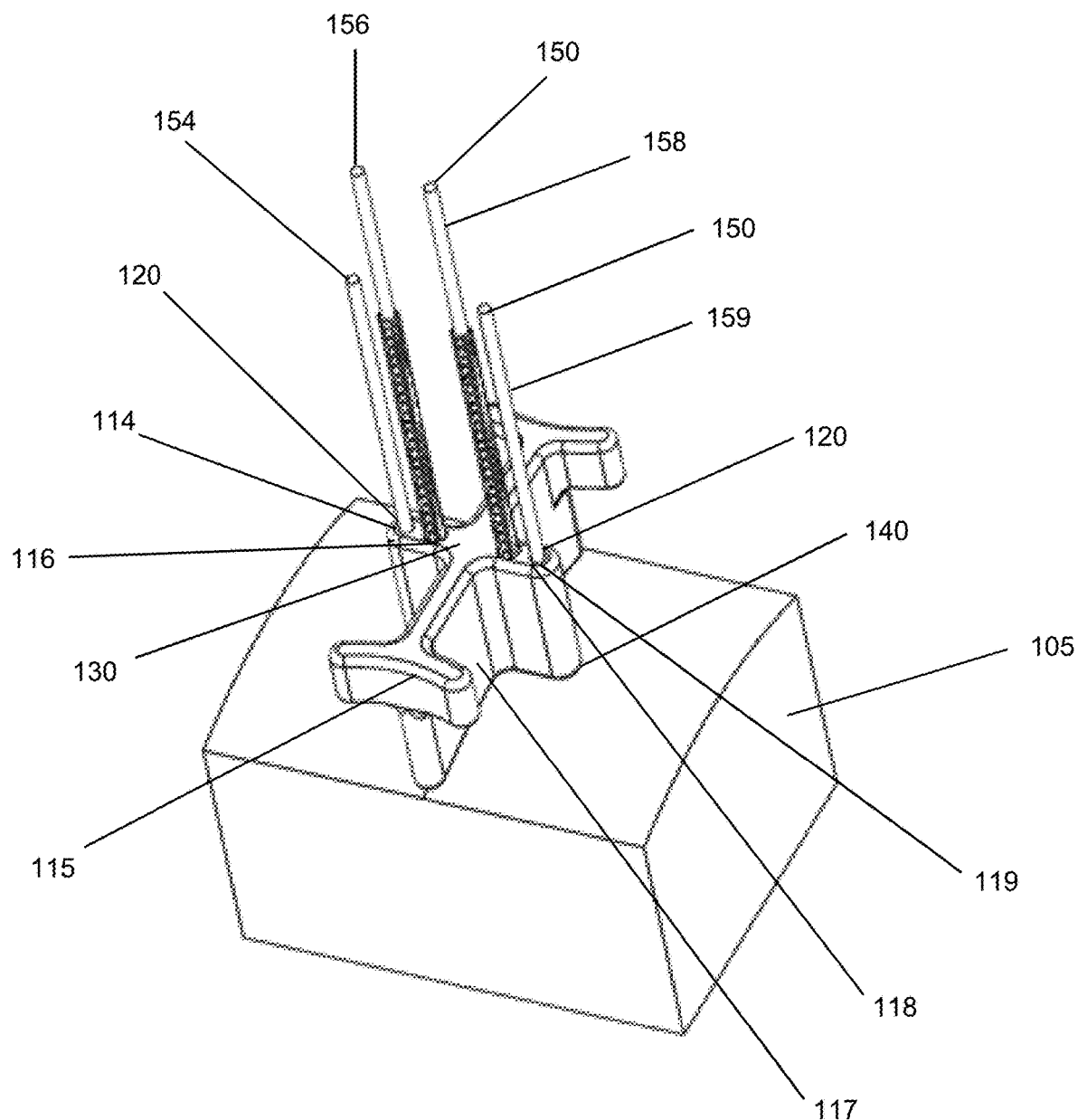
FIG. 1 is a perspective view of an aligning guide receiving guide wires inserted into a bone, in accordance with an aspect of the present invention.

A calcaneal osteotomy system is depicted in various embodiments in FIGS. 1-15. With reference to FIG. 1, an aligning guide 100 is located on a lateral side of a calcaneus 105. Guide 100 may have, for example, a body 117, an arm 115 extending from body 117 and a plurality of wire holes 120 extending from a top side 130 to a bottom side 140 to receive a plurality of guide wires 150 (e.g., K-wires), such that wires 150 may extend through guide 100 into a bone, such as calcaneus 105. Wires 150 may include a first wire 154, a second wire 156, a third wire 158, and a fourth wire 159 received in a first hole 114, a second hole 116, a third hole 118 and a fourth hole 119 of holes 120, respectively, such that the wires and holes are aligned longitudinally along a longitudinal dimension of body 117.

Guide 100 is depicted with four wire holes 120 in FIG. 1; however, the number of wire holes 120 may vary with, for example, bone size, bone density, and/or surgical desire. The wire holes may also be bounded by hole defining surfaces of body 117 such that the bounding surfaces of the holes are of various shapes to receive various shaped wires. The wires received in such holes may also be threaded or smooth. For example, second wire 156 and third wire 158 may have threads for engaging a nut or otherwise engaging other objects. In an example, first wire 154 and fourth wire 159 may be unthreaded. Wire holes 120 are depicted with guide wires 150 inserted, however the number of instances of wire holes 120 with guide wires 150 inserted may vary with, for example, bone size, bone density, and/or surgical desire. Wire holes 120 are depicted as circular, however wire holes 120 may be any shape configured (e.g., shaped and dimensioned) to accommodate guide wires 150 as indicated above. Guide wires 150 may be, for example, inserted through guide 100 into holes drilled into calcaneus 105 or wires 150 may be inserted by hand without such predrilling.

Guide 100 may be used to determine a position for an implant and to insert guide wires 102 to guide or position instruments during a calcaneal osteotomy surgical procedure, for example. As depicted in FIG. 1 and described above, guide wires 150 may include first guide wire 154 and second guide wire 156 positioned towards a posterior of calcaneus 105, and third guide wire 158 and fourth guide wire 159 positioned towards an anterior of calcaneus 105. As a calcaneal osteotomy surgical procedure involves cutting a portion of calcaneus 105, wire holes 120 with inserted guide wires 150 may be positioned on opposing sides of a prospective calcaneal cut. For example, first guide wire 154 and second guide wire 156 may be positioned on a first side of the cut while third guide wire 158 and fourth guide wire 159 may be on a second side of the cut.

Figure 2:
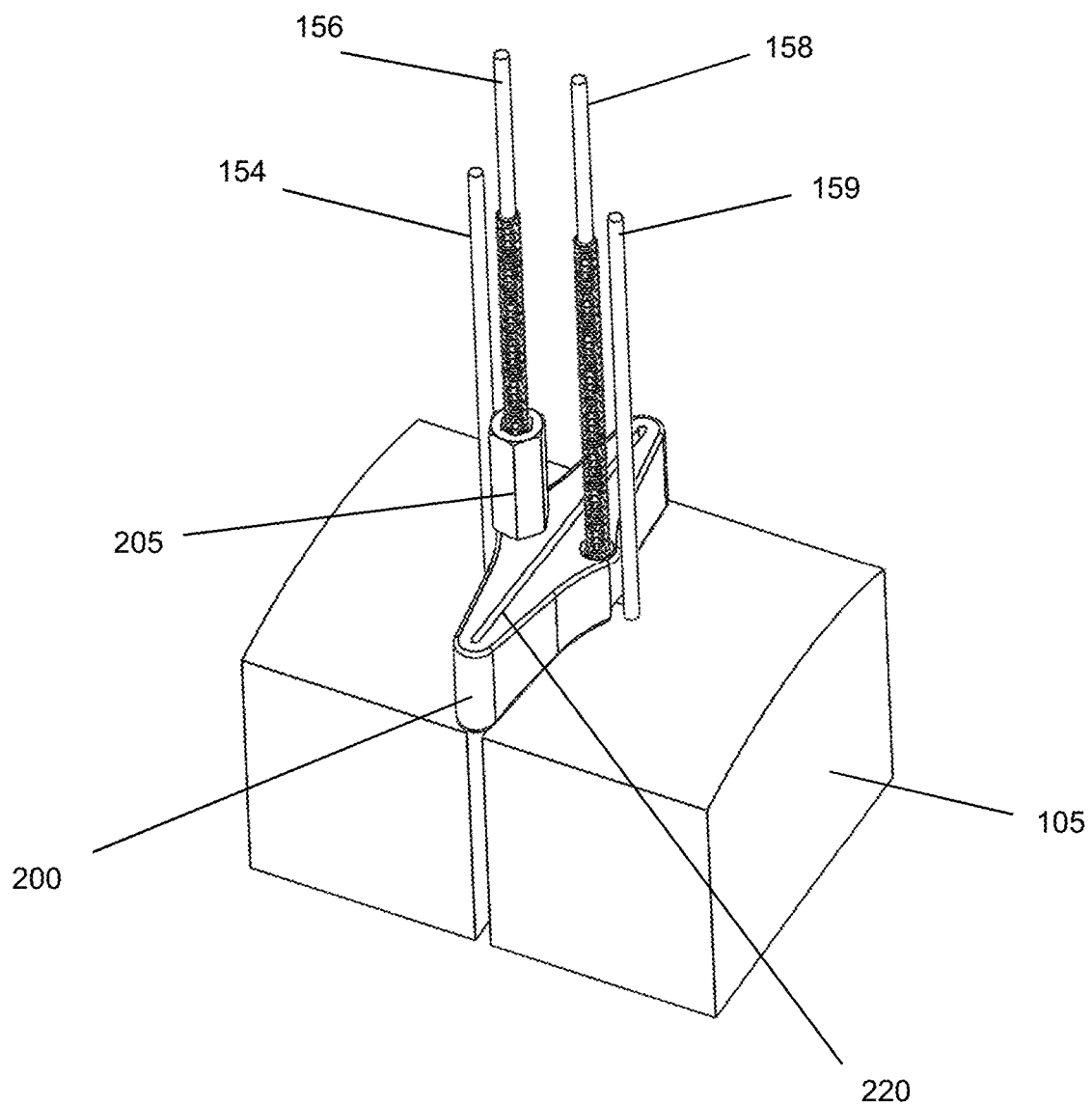
FIG. 2 is a perspective view of a cut guide receiving the guide wires of FIG. 1, in accordance with an aspect of the present invention.
Figure 3:
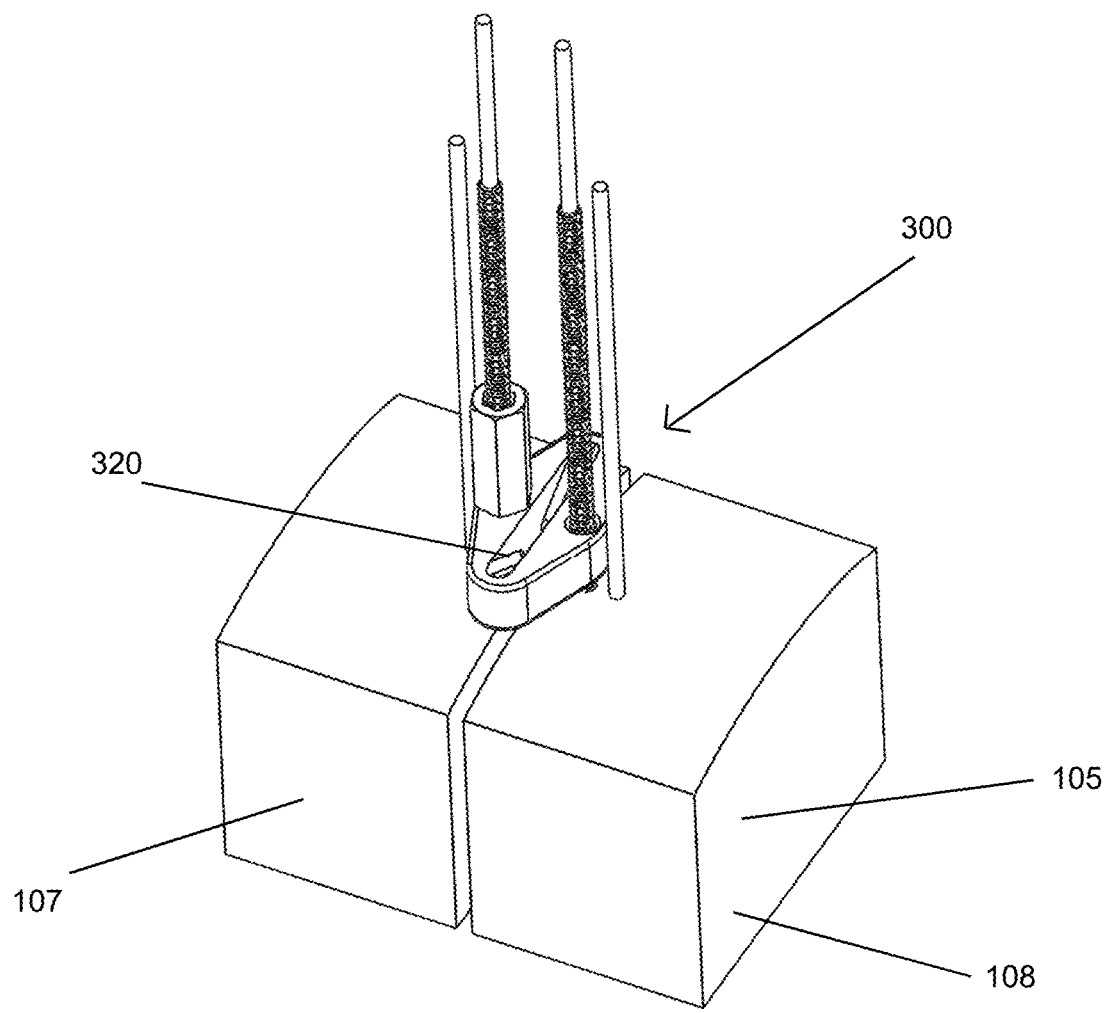
FIG. 3 is a perspective view of a cut guide receiving the guide wires of FIG. 1, in accordance with an aspect of the present invention.

After guide wires 150 are inserted into calcaneus 105 via wire holes 120, guide 100 may be, for example, removed. A cut guide 200 may be received over wires 150 as depicted in FIG. 2. Second wire 156 may be received in a hole (not shown) extending through cut guide 200 and may be threadingly connected to a nut 205. Third wire 158 may be received in a hole (not shown) of cut guide 200 such that third wire 158 extends through cut guide 200. A cut slot 220 may be present between second wire 156 and third wire 158 as depicted in FIG. 2. In another example depicted in FIG. 3, a cut guide 300 may be identical to cut guide 200 except that a burr guide slot 320 may be substituted for cut slot 220. A cut may be made to separate portions of calcaneus 105 via a saw in cut slot 220 (FIG. 2), or a burr in burr guide slot 320 (FIG. 3), into a posterior calcaneal or first portion 107 and an anterior calcaneal or second portion 108 (FIG. 4).

Figure 4:
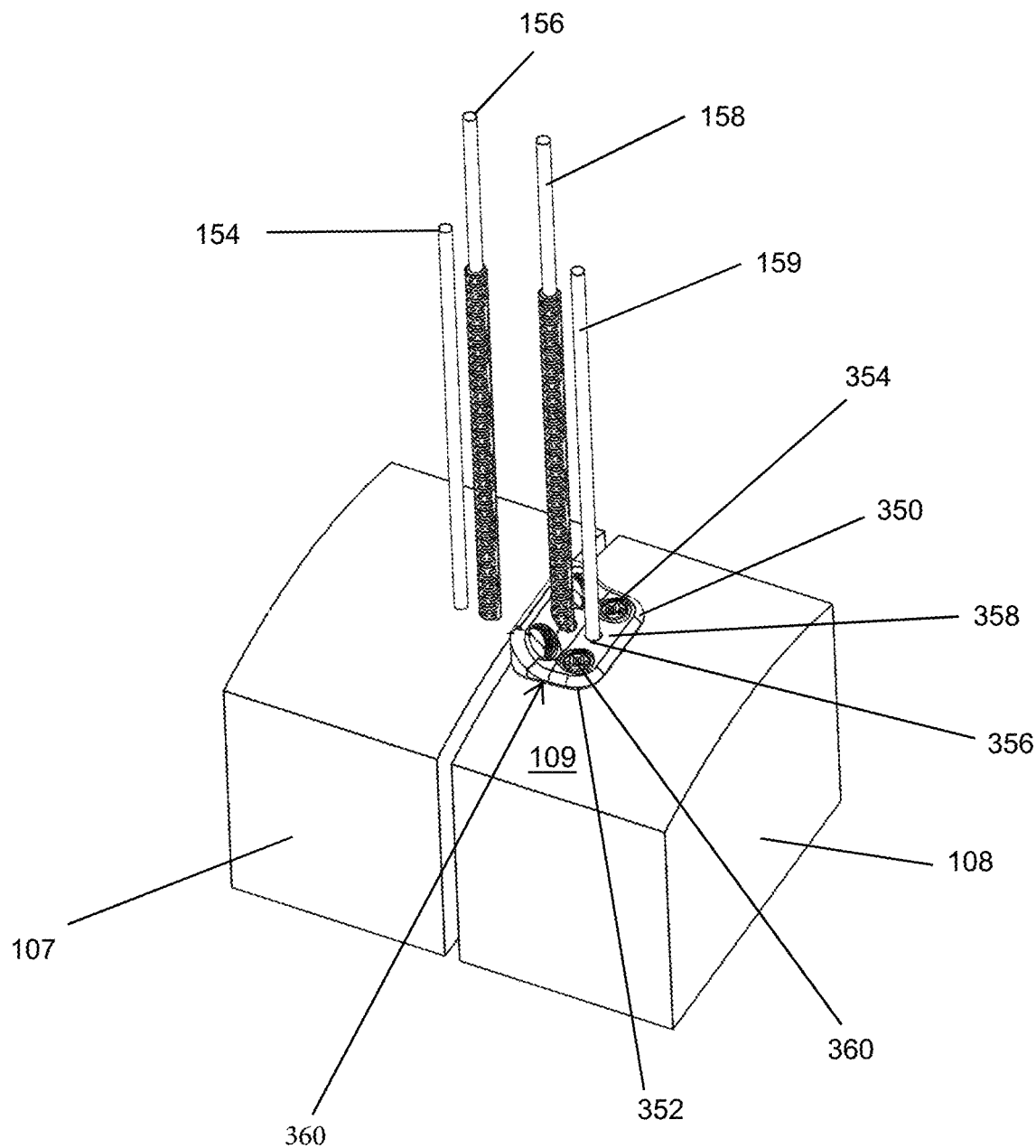
FIG. 4 is a perspective view of an attached implant plate receiving two of the guide wires of FIG. 1 in accordance with an aspect of the present invention.

As depicted in FIG. 4, after cut guide 200, or cut guide 300, may be removed from calcaneus 105 and wires 150, an implant plate 350 having holes 356 and 358 may be received on third wire 158 and fourth wire 159, such that a bottom surface 360 of plate 350 may contact a top surface 109 of second portion 108 of calcaneus 105. Plate 350 may be attached to second portion 108 of calcaneus 105 via screws 372 that extend downwardly (e.g., approximately parallel to wires 150) toward second portion 108 through a first screw hole 352 and a second screw hole 354 such that screws 372 pass through plate 350 and connect plate 350 to second portion 108. Plate 350 may also be configured (e.g., shaped and dimensioned) such that bottom surface 360 has a shape (e.g., a flat surface) complementary to top surface 109 without penetrating or extending into second portion 108.

Figure 5:
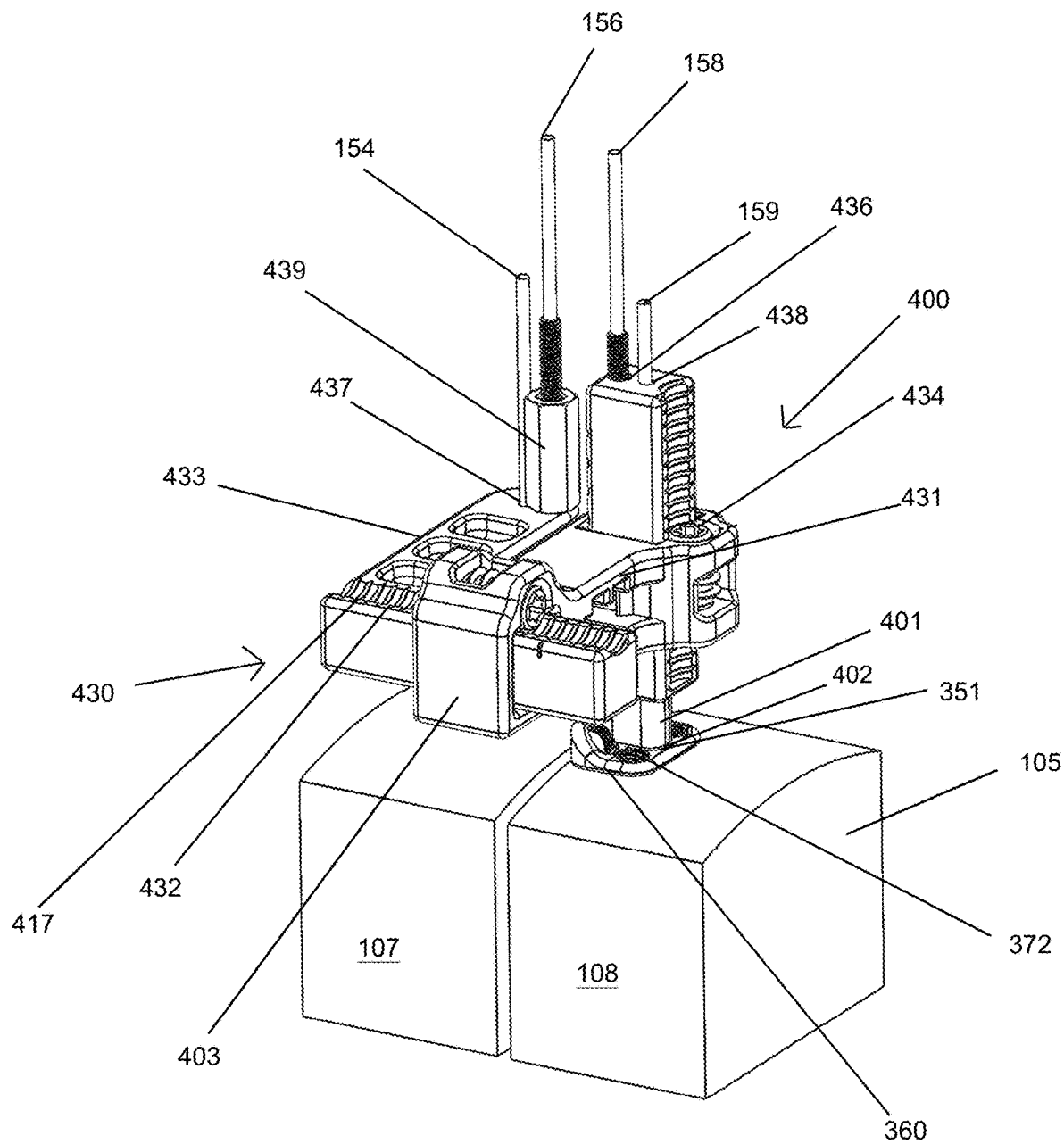
FIG. 5 is a perspective view of a shift jig engaged with the implant plate, in accordance with an aspect of the present invention; and receiving the guide wires, of FIG. 4, in accordance with an aspect of the present invention.
Figure 6:
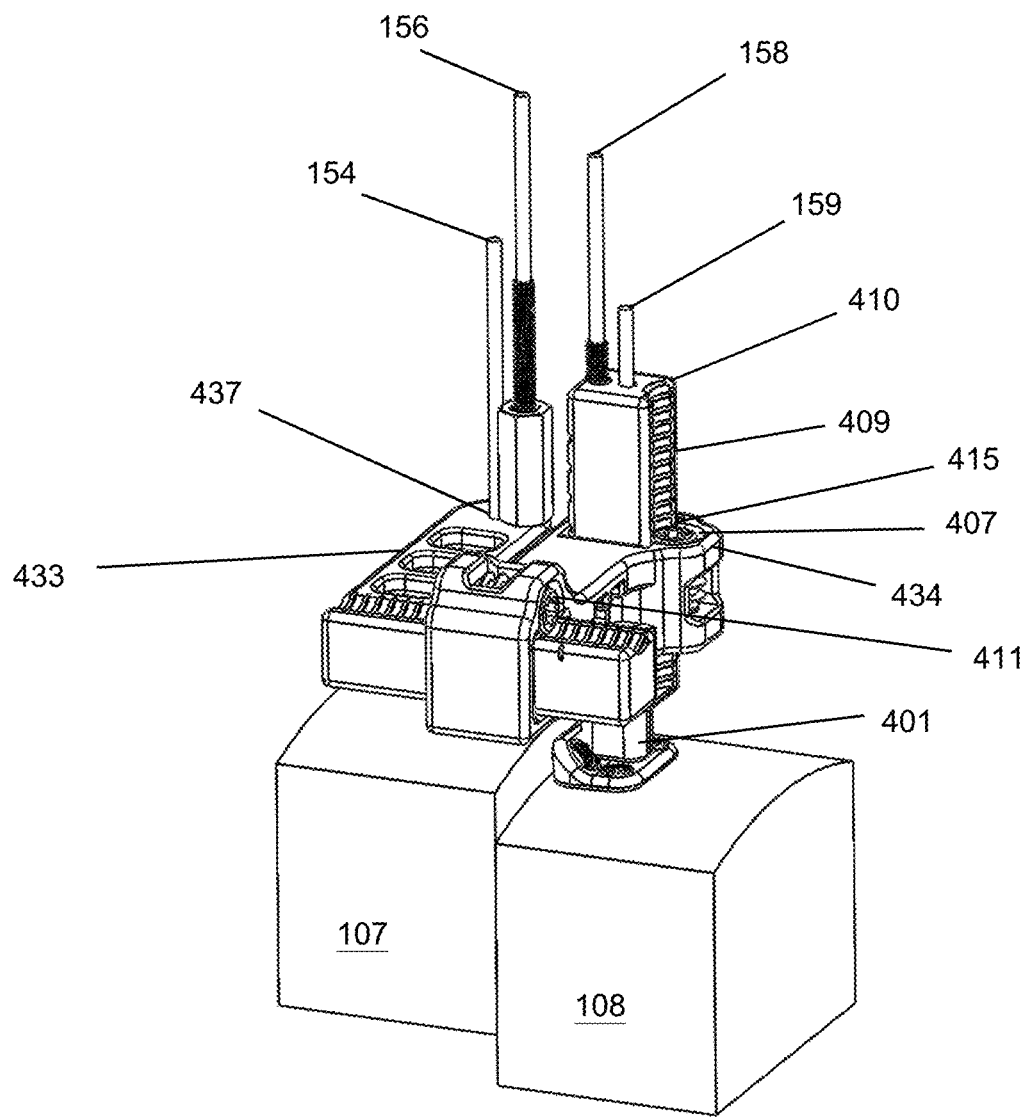
FIG. 6 is a perspective view of the shift jig of FIG. 5 with portions of the bone compressed and displaced, in accordance with an aspect of the present invention.
Figure 7:
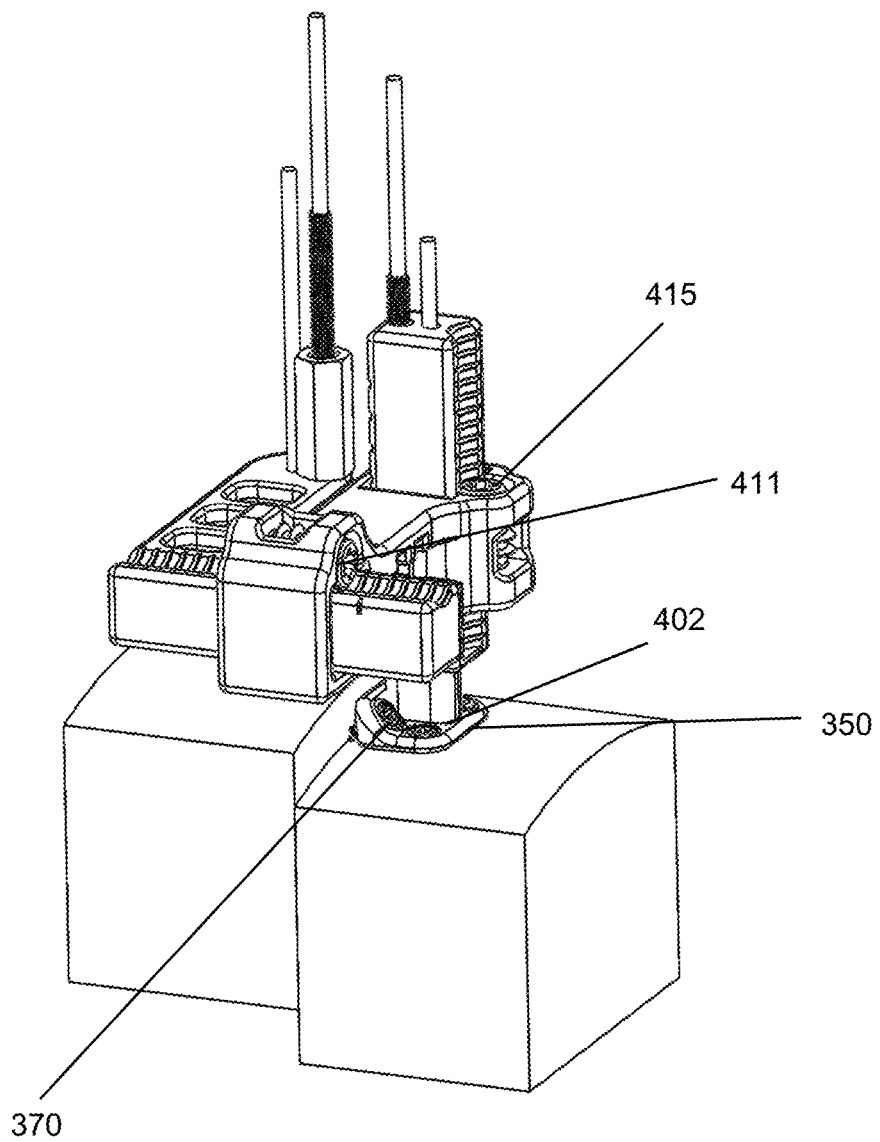
FIG. 7 is a perspective view of the shift jig of FIG. 6 with screws through the implant plate into the bone in accordance with an aspect of the present invention.

As depicted in FIGS. 5-7, a bone adjustment mechanism or shift jig 400 may be positioned such that first guide wire 154 is received in a first hole 437, second guide wire 156 received in a second hole 440 (FIG. 14), and third guide wire 158 received in a third hole 436 and fourth guide wire 159 is received in a fourth hole 438 of jig 400. A first leg or coupler 401 of shift jig 400 may extend downwardly from a remainder (e.g., from first arm) of shift jig 400 and may be placed onto and/or connected to a top surface 351 of plate 350. Top surface 351 and a bottom end 402 of coupler 401 may be shaped complementarily (e.g., formed as flat surfaces) to facilitate an engagement or connection therebetween. A nut 439 may be connected to first guide wire 154 to connect jig 400 to first portion 107 of calcaneus 105 through second hole 440 in a second leg 601 (FIG. 9) which may extend from body of jig 400 to contact first bone portion 107.

Shift jig 400 may have, for example, a body 430 formed of a first arm or segment 431 approximately perpendicular to a second arm or segment 432, a third arm or segment 433 approximately perpendicular to second segment 432, a fourth arm or segment 434 approximately perpendicular to first segment 431 and an open interior or cavity (sometimes present) between the four segments. Fourth segment 434 may, for example, extend from first segment 431 towards third segment 433 but does not contact third segment 433, leaving an opening.

Coupler 401 may extend downwardly to contact plate 350 from first segment 431, for example. Second leg 601 may extend downwardly to contact first bone portion 107 from second segment 433, for example. In other examples, coupler 401 and/or second leg 601 may extend downwardly from other portions of body 430 to contact, engage and/or couple with first bone portion 107 and/or second bone portion 108.

Figure 14:
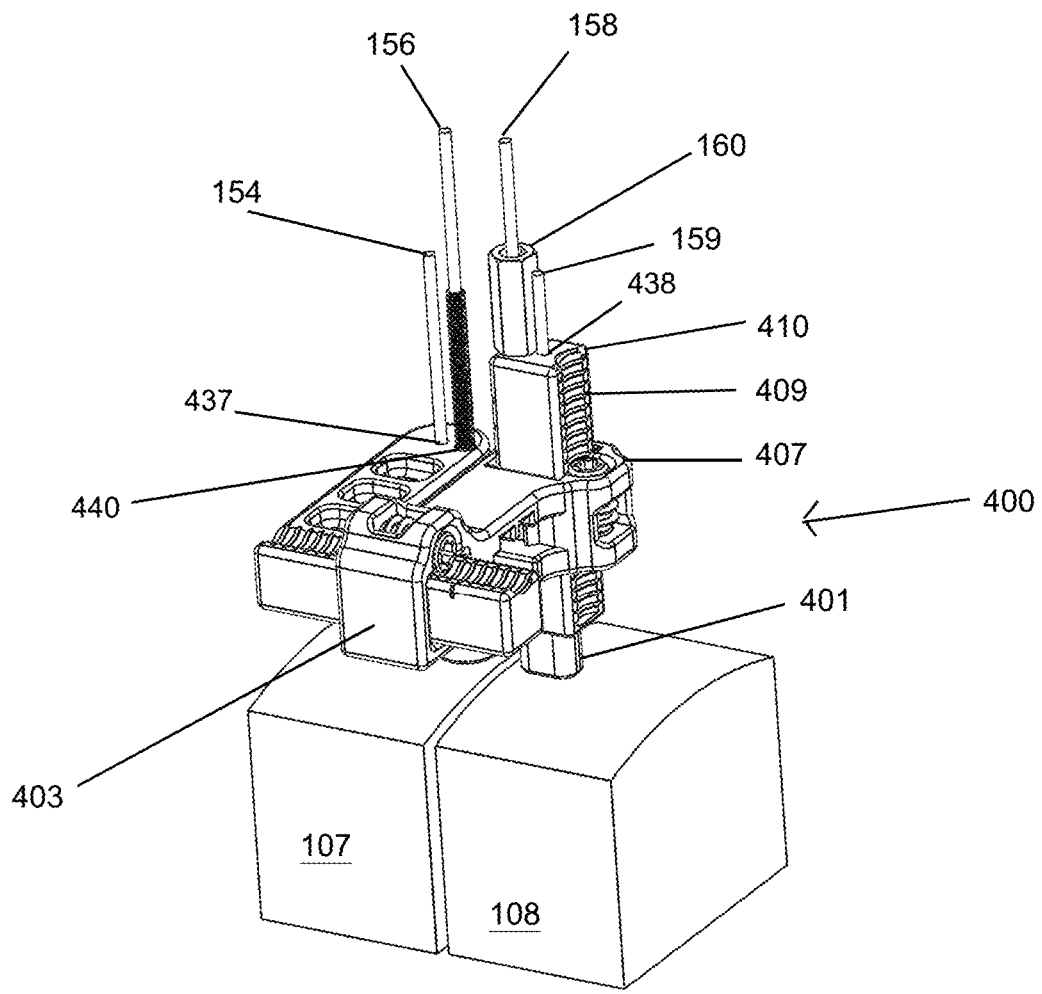
FIG. 14 is a perspective view of a shift jig engaged with the bone, and receiving the guide wires of FIG. 1, in accordance with an aspect of the present invention.

Shift jig 400 may have, for example, a compression-distraction fixture 403 and a displacement fixture 409 as depicted in FIGS. 5-7. Compression-distraction fixture 409 may be movably coupled with and on opposing sides of third segment 433. Displacement fixture 409 may be movably coupled to a guide segment 407. Coupler 401 may be connected to and extend away from fourth segment 434 in an approximately perpendicular direction relative to a longitudinal dimension of fourth segment 434 and towards calcaneus 105. Third hole 436 and fourth hole 438 extend through fourth segment 434 and through coupler 401, with first guide wire 154 passing through first hole 437 and second guide wire 156 passing through second hole 440 (FIG. 14). Third hole 436 extends through guide segment 407 with fourth guide wire 159 passing therethrough, and with guide segment 407 positioned on second portion 108. While first segment 431, second segment 432, third segment 433, and fourth segment 434 of body 430 of shift jig 400 are depicted, other embodiments of a shift jig may, for example, have configurations with more segments or less segments and such segments may, for example, have configurations forming a body (e.g., body 430) of a shift jig (e.g., shift jig 400) with a different shaped configuration. While shift jig 400 is depicted as having segments arranged in a square shape, other segment configurations may be used to form shift jig and body thereof having different shapes. Although coupler 401 is described as connecting to fourth segment 434, a coupler could be connected to a different portion of jig 400 and extend downwardly therefrom.

With reference to FIGS. 5-7, compression-distraction fixture 403 may have a housing 406 receiving a first power screw 411. Second segment 432 may, for example, have a rack 417 along the length of on an exterior side, with compression-distraction fixture 403 engaged with rack 417 and with first power screw 411 acting as a worm gear movably coupled with rack 417. Compression-distraction fixture 403 may be, for example, movable along rack 417 by actuating first power screw 411 manipulated by a screwdriver (not shown).

Guide segment 407 may be coupled to a threaded rack post 410, with guide segment 407 and/or rack post 410 seated on second portion 107 as depicted in FIG. 6, for example. Displacement fixture 409 includes a housing 408 receiving a second power screw 415. Displacement fixture 409 may be, for example, connected to fourth segment 434 and located on a side of first segment 431 opposite compression-distraction fixture 403. Housing 408 of displacement fixture 409 may be, for example, engaged with rack post 410 and with second power screw 415 acting as a worm gear movably coupled with rack post 410. Displacement fixture 409 may be, for example, movable along rack post 410 by actuating second power screw 415 manipulated by a screwdriver, for example, and thereby moving a remainder of shift jig 400 along rack post 410.

Manipulating first power screw 411 may, for example, move first portion 107 in an approximately anterior/posterior direction providing compression or distraction. Manipulating power screw 415 may, for example, move shift jig 400 and first portion 107 in an approximately medial/lateral direction providing for displacement of first portion 107 relative to second portion 108. Both compression-distraction fixture 403 and displacement fixture 409 may, for example, maintain, or even lock, their position when a screwdriver is not engaged with first power screw 411 or second power screw 415, respectively.

In an example depicted in FIG. 6, first portion 107 and second portion 108 may be displaced vertically relative to each other by driving displacement or power screw 415 of displacement fixture 409. First portion 107 and second portion 108 may be compressed relative to each other by driving first power screw 411 of compression-distraction fixture 403.

Figure 8:
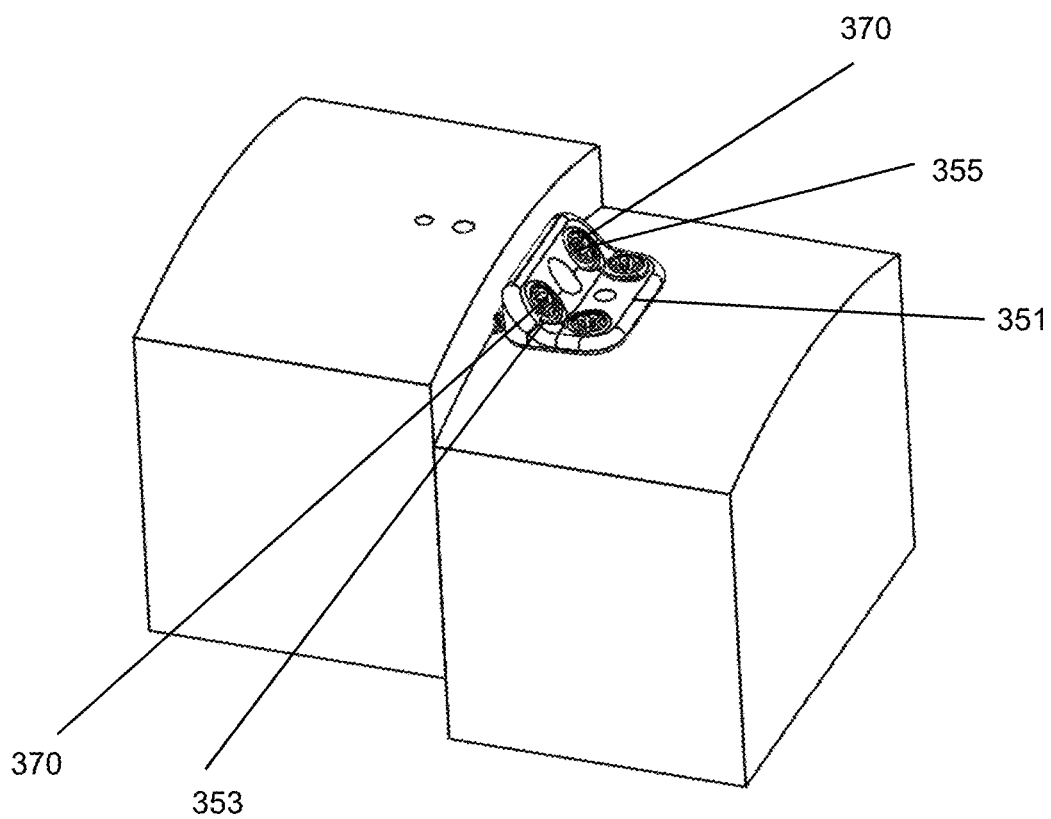
FIG. 8 is a perspective view of the implant plate of FIG. 8 connected to the bone with the jig and wires removed, in accordance with an aspect of the present invention.

As depicted in FIGS. 7-8, screws 370 may be inserted through a first holding hole 353 and a second holding hole 355 in plate 350 at an angle (e.g., an acute angle) relative to screws 372 (described above) to attach plate 350 to first portion 107 to hold first portion 107 and second portion 108 in a desired position relative to each other after the vertical displacement and compression described above. Prior to such insertion of screws 370, holes may be predrilled or the screws may be threaded into calcaneus 105 without predrilling. Further, plate 350 may have a vertically extending portion 651 and a horizontally extending portion 652 to receive screws 372 and screws 370, respectively, for example.

After first portion 107 and second portion 108 are secured in a desired position relative to each other via plate 350, screws 370 and screws 372, jig 400 may be removed from wires 150 followed by wires 150 being removed from calcaneus 105 as depicted in FIG. 8.

Figure 9:
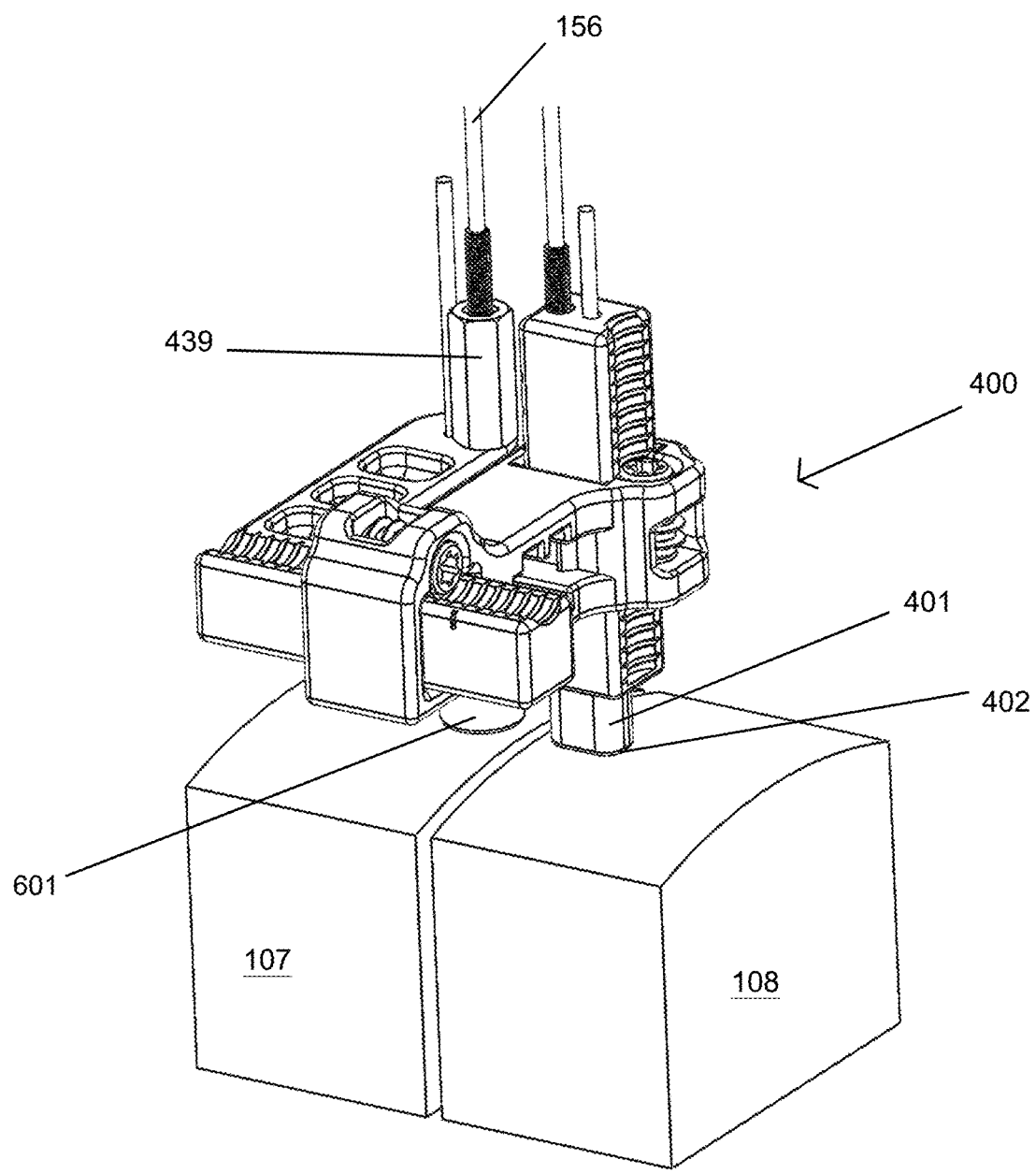
FIG. 9 is a perspective view of a shift jig engaged with the bone, and receiving the guide wires of FIG. 1, in accordance with an aspect of the present invention.

In an example depicted in FIG. 9, after calcaneus 105 is cut using cut guide 200 or cut guide 300 as described above relative to FIGS. 2-3, instead of connecting plate 350 to second portion 108, jig 400 may be received on wires 150 as depicted in FIG. 7 and as described above. Coupler 401 may be received on second portion 108, instead of being received on plate 350 as described above. Bottom end 402 of coupler 401 may be configured (e.g., shaped and dimensioned) to facilitate an engagement with second portion 108 instead of engaging plate 350 as described above. Second wire 150 may be threadingly connected to nut 439 to secure jig 400 relative to calcaneus 105.

Figure 10:
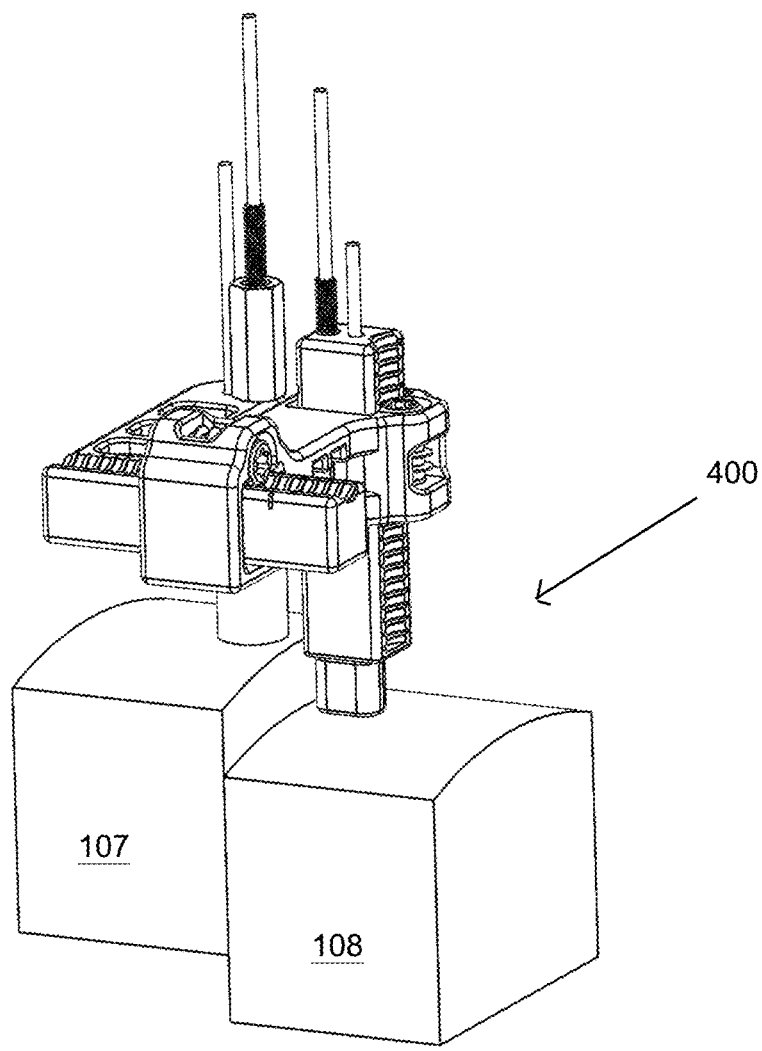
FIG. 10 is a perspective view of the shift jig of FIG. 9 with portions of the bone compressed and displaced, in accordance with an aspect of the present invention.

As described above, first portion 107 and second portion 108 may be moved vertically relative to each other and compressed or distracted relative to each other using displacement fixture 409 and compression-distraction fixture 403, as depicted in FIG. 10.

Figure 11:
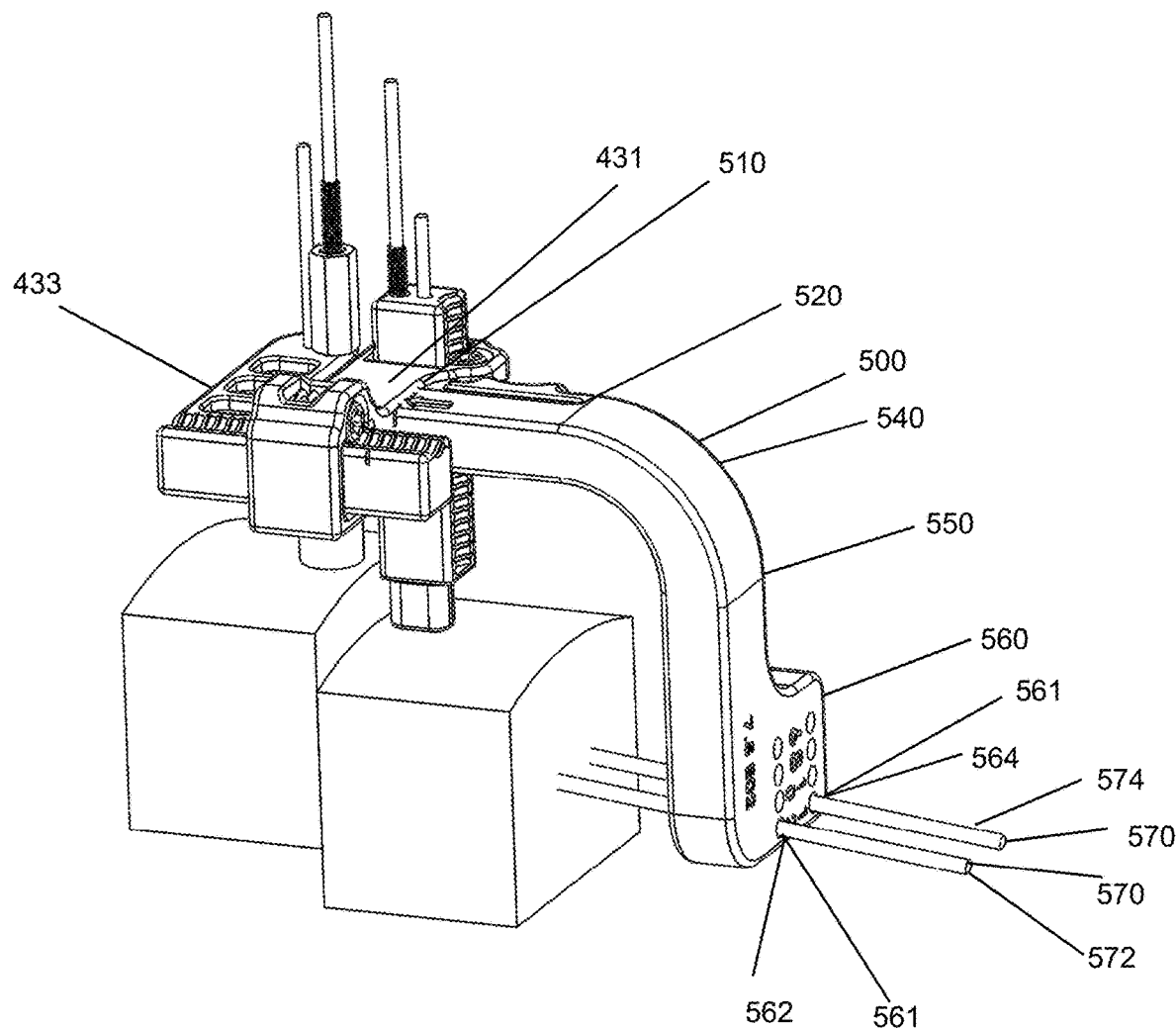
FIG. 11 is a perspective view of the shift jig of FIG. 10 coupled to an outrigger receiving outrigger guide wires, in accordance with an aspect of the present invention.

As depicted in FIG. 11, an outrigger 500 may be connected to jig 400, such as by being received in an opening 510 of first segment 431, for example. Outrigger 500 may include a fifth arm or segment 520 in a substantially same plane as first segment 431, second segment 432, third segment 433 and fourth segment 434 described above. Fifth segment 520 may extend away from third segment 433 and may be connected to a downwardly depending member 550 by a curved portion 540, such that downwardly depending member 550 has a longitudinal dimension aligned about perpendicularly to first segment 431, and such that member 550 extends along a side of second portion 108 of calcaneus 105. A wire receiving member 560 may be connected to downwardly depending member 550 and may include wire receiving openings 561, such as a first outrigger opening 562 and a second outrigger opening 564, to receive outrigger wires 570, such as a first outrigger wire 572 and a second outrigger wire 574. Wires 570 may extend through wire receiving member 560 into first portion 107 and second portion 108. Prior to inserting the wires, holes may be pre-drilled in calcaneus 105 to facilitate entry of the wires. In other examples, an outrigger similar to outrigger 500 could be shaped and dimensioned differently while still aligning outrigger wires in a same manner as outrigger 500.

Figure 12:
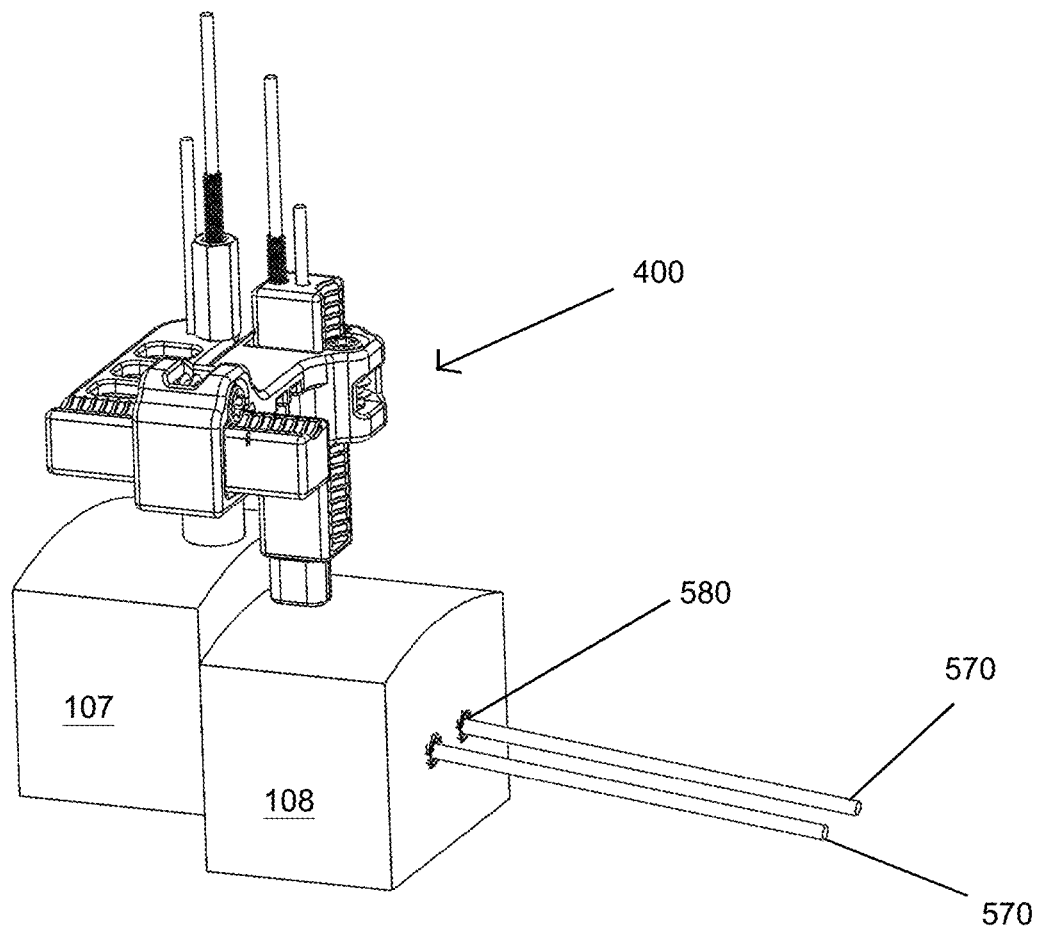
FIG. 12 is a perspective view of the shift jig of FIG. 11 with the outrigger removed and the outrigger guide wires remaining, in accordance with an aspect of the present invention.
Figure 13:
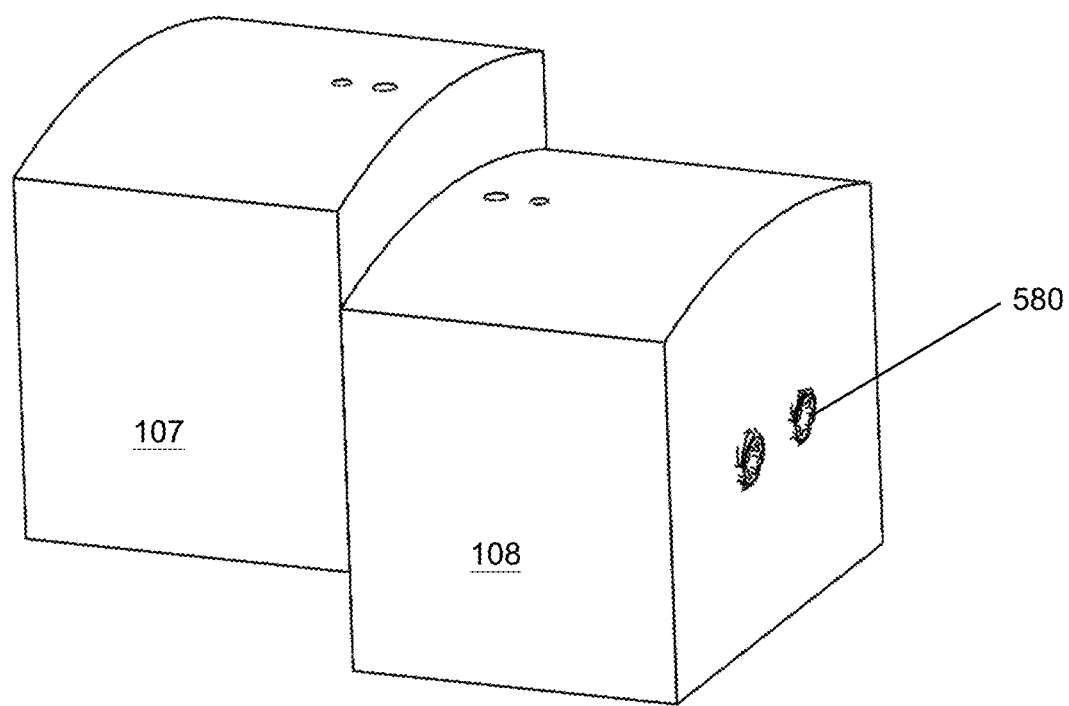
FIG. 13 is a perspective view of the shift jig of FIG. 12 with cannulated screws located around the outrigger guide wires in the bone, in accordance with an aspect of the present invention.

As depicted in FIG. 12, outrigger 500 may be removed from outrigger wires 570 and separated from jig 400 leaving wires 570. Cannulated screws 580 may be received on outrigger wires 570 and may be driven into first portion 107 and second portion 108 to connect first portion 107 and second portion 108 as depicted in FIG. 13. Jig 400 and wires 570 may be removed thereby leaving cannulated screws 580 holding first portion 107 relative to second portion 108 as depicted in FIG. 13.

Figure 15:
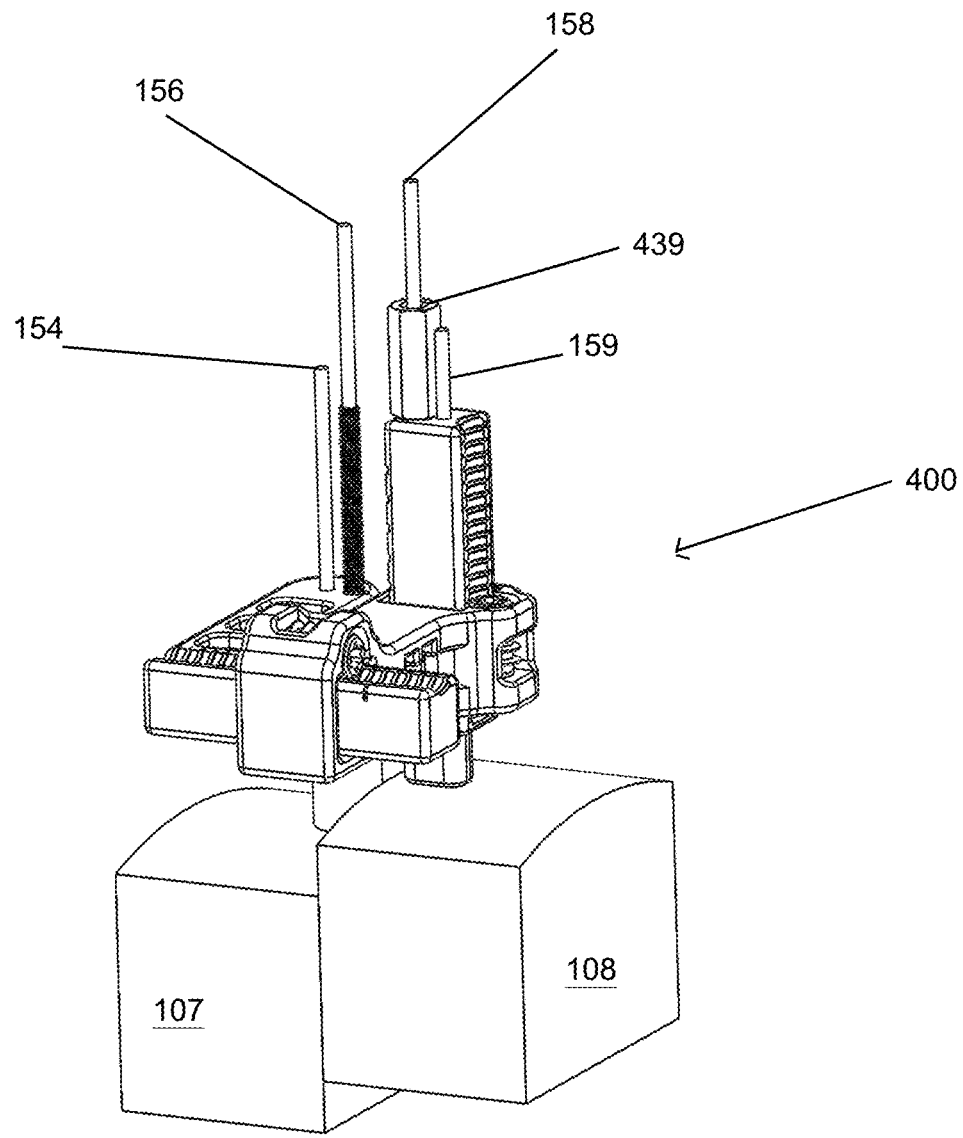
FIG. 15 is a perspective view of the shift jig of FIG. 14 with portions of the bone compressed and displaced, in accordance with an aspect of the present invention.

In an example depicted in FIGS. 14-15, after calcaneus 105 is cut using cut guide 200 or cut guide 300 as described above relative to FIGS. 2-3, jig 400 may be received on wires 150 as depicted and described above relative to FIGS. 9-10. Coupler 401 may be received on second portion 108 instead of on plate 350 as described above. More specifically, bottom end 402 of coupler 401 may be configured (e.g., shaped and dimensioned) to facilitate an engagement with second portion 108. Instead of nut 439 being threaded on second wire 156, a nut 160 may be threaded on third wire 158 to secure jig 400 relative to calcaneus 105.

As described above, first portion 107 and second portion 108 may be moved vertically relative to each other and compressed or distracted relative to each other using displacement fixture 409 and compression-distraction fixture 403, as depicted in FIG. 14. For example, second portion 108 may be raised vertically relative to first portion 107 via displacement fixture 409 due to the attachment of nut 160 to third wire 158 securing second portion thereto such that upward movement of displacement fixture 409 along rack post 410 by actuating second power screw 415 manipulated by a screwdriver, for example, may thereby move second portion 108 upwardly relative to first portion 107.

As described above shift jig 400 may be configured (e.g., shaped, dimensioned, or otherwise arranged) for use with calcaneal osteotomies. However, the devices and procedures may be configured (e.g., shaped, dimensioned, and otherwise arranged) for use with bone osteotomy procedure that involves compression/distraction and lateral/medial positioning and fixation. Furthermore, shift jig 400 may be configured (e.g., shaped, dimensioned, and otherwise arranged) for use in bone osteotomy procedures that involve compression/distraction and dorsal/plantar positioning and fixation. Still further, shift jig 400, may be configured (e.g., shaped, dimensioned, and otherwise arranged) for use in bone osteotomy procedures that involve compression/distraction and any relative transverse bone positioning and fixation.

While several aspects of the present invention have been described and depicted herein, alternative aspects may be affected by those skilled in the art to accomplish the same objectives. Accordingly, it is intended by the appended claims to cover all such alternative aspects as fall within the true spirit and scope of the invention.

We claim:

1. A bone displacement system comprising:
a body having a first arm and a second arm;
said first arm connected to a first leg configured to be located on a first bone portion;
said second arm connected to a second leg configured to be connected to a second bone portion;
a force application fixture coupled to said first arm and said first leg and configured to apply a force between said first arm and said first leg;
wherein said body is connected to an outrigger arm, said outrigger arm configured to extend from said body and away from said body such that said outrigger arm is configured to extend along said first bone portion, said outrigger arm having an opening for aligning a screw such that the screw connects the first bone portion to the second bone portion; and
wherein the applying the force by said force application fixture between said first arm and said first leg comprises applying the force to displace said first bone portion relative and said second bone portion relative to each other.

2. The system of claim 1 wherein said opening is configured to receive a wire configured to connect to the first bone and the system further comprises a cannulated screw configured to be received on said wire and configured to connect the first bone to the second bone.

3. The system of claim 1 wherein said second leg comprises an opening therethrough configured to receive a wire to connect said second leg and said second arm to the second bone.

4. The system of claim 3 further comprising a cut guide configured to receive a wire to align the cut guide to cut a bone.

5. The system of claim 1 wherein said first leg comprises an opening therethrough configured to receive a wire to connect said first leg and said first arm to the first bone, said system comprising a plate comprising a plate wire opening configured to receive the wire to align the plate relative to the first bone portion and the second bone portion.

6. The system of claim 1 wherein said system comprises a plate comprising a non-penetrating bottom surface configured to contact a top surface of the first bone portion without penetrating the first bone portion.

7. The system of claim 1 wherein said first leg extends downwardly from said first arm and said second leg extends downwardly from said second arm.

8. The system of claim 1 further comprising a second force application fixture configured to apply a second force between said body and said second leg.

9. A method for use in displacing a bone, comprising:
coupling a first arm of a body to a first bone portion via a first leg connected to the body, the first leg engaging the first bone portion;
coupling a second arm of the body to a second bone portion via a second leg connected to the body;
applying a force between the first arm and the first leg via a force application fixture coupled to the first arm and the first leg to move the first bone portion relative to the second bone portion;
wherein said body is connected to an outrigger arm, and further comprising extending said outrigger arm from said body and away from said body such that said outrigger arm extends along said first bone portion, said outrigger arm having an opening for aligning a screw such that the screw connects the first bone portion to the second bone portion; and
wherein the applying the force by said force application fixture between said first arm and said first leg comprises applying the force to displace said first bone portion relative to said second bone portion.

10. The method of claim 9 wherein the coupling the first arm to the first bone portion comprises connecting a wire to the first bone portion and receiving the wire in an opening through said first leg.

11. The method of claim 2 further comprising receiving a wire in the opening of the outrigger arm to connect said outrigger arm to said first bone portion.

12. The method of claim 11 further comprising removing said outrigger arm from said wire, receiving a screw over said wire and connecting said first bone portion to said second bone portion by said screw.

13. The method of claim 9, further comprising locating the first leg on the first bone portion, said locating comprising locating an entire bottom surface of a plate on an upper exterior surface of said first bone portion without penetrating said first bone portion and the method further comprising connecting the plate to the first bone portion or the second bone portion by a second plate screw in a second plate opening prior to the moving the first bone portion relative to the second bone portion.

14. The method of claim 9 further comprising applying a second force between the body and the second leg by a user using a second force application fixture.

15. The method of claim 9 wherein the coupling the first arm of the body to the first bone portion comprises connecting said first arm to the first bone by a wire through an opening in said first leg.

16. The method of claim 15 further comprising receiving an opening of a cut guide on a wire.

17. The method of claim 15 further comprising aligning, a plate relative to the first bone portion and the second bone portion.

* * * * *

UNITED STATES PATENT AND TRADEMARK OFFICE
CERTIFICATE OF CORRECTION

| | | |
|---|---|---|
| PATENT NO. | : 11,903,598 B2 | |
| APPLICATION NO. | : 17/462719 | |
| DATED | : February 20, 2024 | |
| INVENTOR(S) | : Coyne et al. | |

It is certified that error appears in the above-identified patent and that said Letters Patent is hereby corrected as shown below:

In the Claims

Column 9, Line 5 Claim 11, Delete "claim 2" and insert -- claim 9 --

Signed and Sealed this
Twenty-sixth Day of March, 2024

Katherine Kelly Vidal
*Director of the United States Patent and Trademark Office*